United States Patent
Pyun et al.

(10) Patent No.: US 12,400,329 B2
(45) Date of Patent: Aug. 26, 2025

(54) SKIN CANCER DIAGNOSIS METHOD BASED ON IMAGE ANALYSIS USING ARTIFICIAL INTELLIGENCE

(71) Applicant: SPECLIPSE, INC., Gyeonggi-do (KR)

(72) Inventors: Sung Hyun Pyun, Seoul (KR); Wan Ki Min, Gyeonggi-do (KR)

(73) Assignee: SPECLIPSE, INC., Gyeonggi-Do (KR)

( * ) Notice: Subject to any disclaimer, the term of this patent is extended or adjusted under 35 U.S.C. 154(b) by 424 days.

(21) Appl. No.: 18/065,832

(22) Filed: Dec. 14, 2022

(65) Prior Publication Data
US 2024/0013394 A1    Jan. 11, 2024

(30) Foreign Application Priority Data

Jul. 11, 2022   (KR) ........................ 10-2022-0147037

(51) Int. Cl.
*G06K 9/00*     (2022.01)
*G06N 3/04*     (2023.01)
*G06T 7/00*     (2017.01)

(52) U.S. Cl.
CPC .............. *G06T 7/0014* (2013.01); *G06N 3/04* (2013.01); *G06T 2207/20081* (2013.01);
(Continued)

(58) Field of Classification Search
CPC ......... G06T 7/0014; G06T 2207/20081; G06T 2207/20084; G06T 2207/30088; G06T 2207/30096; G06T 2207/30196; G06N 3/04; G06N 3/045; G06N 3/08; G06N 20/00; G16H 50/20; G16H 50/30;
(Continued)

(56) References Cited

U.S. PATENT DOCUMENTS

2021/0350112 A1    11/2021    Jenoski et al.

FOREIGN PATENT DOCUMENTS

| CN | 106504232 A | * | 3/2017 | ........... G06N 3/0454 |
| CN | 107680678 A | * | 2/2018 | ........... G06K 9/4671 |

(Continued)

OTHER PUBLICATIONS

International Search Report from corresponding PCT Application No. PCT/KR2022/020576, dated Jul. 31, 2023.
(Continued)

*Primary Examiner* — Xin Jia
(74) *Attorney, Agent, or Firm* — Harness, Dickey & Pierce, P.L.C.

(57) ABSTRACT

Provided is a disease information providing method including obtaining first image data obtained by image-capturing a body part and one or more suspicious tissues located in the body part, analyzing the first image data using an artificial neural network, detecting at least one target tissue from among the one or more suspicious tissues included in the first image data on the basis of the analysis result, requesting second image data on the at least one target tissue, obtaining the second image data obtained by image-capturing the at least one target tissue, obtaining disease information, wherein the second artificial neural network is trained to obtain a target result value related to the plurality of disease indicators for the target tissue included in the image data, and providing a disease score on the basis of the target result value.

10 Claims, 15 Drawing Sheets

(52) U.S. Cl.
CPC .............. *G06T 2207/20084* (2013.01); *G06T 2207/30088* (2013.01); *G06T 2207/30096* (2013.01); *G06T 2207/30196* (2013.01)

(58) Field of Classification Search
CPC ........ G16H 50/70; G16H 30/40; G16H 30/20; G16H 50/50; G16H 70/00; A61B 5/441; G06V 10/82; G06V 20/70; G06V 2201/03
See application file for complete search history.

(56) References Cited

FOREIGN PATENT DOCUMENTS

| | | | | | |
|---|---|---|---|---|---|
| CN | 108564578 | A | | 9/2018 | |
| CN | 112584749 | A | * | 3/2021 | ......... A61B 1/00009 |
| CN | 112950569 | A | * | 6/2021 | ........... G06K 9/6256 |
| KR | 10-2020-0101540 | A | | 8/2020 | |
| KR | 10-2222509 | B1 | | 3/2021 | |
| KR | 10-2022-0070816 | A | | 5/2022 | |
| KR | 10-2410545 | B1 | | 6/2022 | |
| WO | WO-2021094507 | A1 | * | 5/2021 | ........... G06K 9/0014 |
| WO | WO-2021/216721 | A1 | | 10/2021 | |

OTHER PUBLICATIONS

Extended European Search Report from corresponding European Application No. 22213411.6, dated Aug. 16, 2023.

\* cited by examiner

200

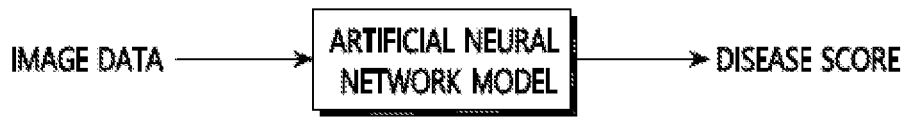

FIG.7

| PATHOLOGICAL INDICATOR | DETAILED PATHOLOGICAL INDICATOR | DISEASE SCORE | TYPE SCORE | TOTAL SCORE |
|---|---|---|---|---|
| MALIGNANT | MALIGNANT MELANOMA | M1 | Mt1 | T |
| | BASAL CELL CANCER | M2 | | |
| | SQUAMOUS-CELL CANCER | M3 | | |
| PRE-MALIGNANT | ACTINIC KERATOSIS | P1 | Pt1 | |
| | ATYPICAL NEVUS SYNDROME | P2 | | |
| | GIANT PIGMENTED NEVUS | P3 | | |
| BENIGN | ANEPIDERMAL CYST | B1 | Bt1 | |
| | WART | B2 | | |
| | SEBORRHEIC KERATOSIS | B3 | | |
| | MILIUM | B4 | | |
| | SEBACEOUS HYPERPLASIA | B5 | | |
| | DERMATOFIBROMA | B6 | | |
| | MOLE | B7 | | |
| | CORN | B8 | | |
| | CALLUS | B9 | | |
| | FRECKLE | B10 | | |

FIG.8

SKIN CANCER DIAGNOSIS METHOD BASED ON IMAGE ANALYSIS USING ARTIFICIAL INTELLIGENCE

CROSS-REFERENCE TO RELATED APPLICATION

This application claims priority to and the benefit of Korean Patent Application No. 10-2022-0147037, filed on Nov. 7, 2022, the disclosure of which is incorporated herein by reference in its entirety.

FIELD

The present disclosure relates to a skin cancer diagnosis method based on image analysis using artificial intelligence that uses image analysis, and a server for performing same.

BACKGROUND

In the field of modern medical technology, there is an increasing demand for various techniques for more accurately performing diagnosis in a non-invasive manner that minimizes inconvenience of the existing biopsy.

In the trend, a method capable of conveniently determining pathological information of a lesion using image data obtained by image-capturing an appearance of the lesion is spotlighted.

SUMMARY

The present disclosure is directed to providing a method of providing disease information related to a lesion using image data, which is obtained by capturing an image of the lesion using an artificial neural network, and a diagnosis device for performing the same.

According to an aspect of the present disclosure, there is provided a disease information providing method performed by an analysis server including a memory and a processor configured to drive a program loaded from the memory, the method including obtaining first image data obtained by image-capturing a body part and one or more suspicious tissues located in the body part, analyzing the first image data using an artificial neural network, wherein the first artificial neural network is trained to detect a target tissue related to a disease from the image data obtained by image-capturing the body part, detecting one or more target tissues, in which a detection score derived from a result value of at least some of a plurality of disease indicators is analyzed to be greater than or equal to a threshold value, from among the one or more suspicious tissues included in the first image data on the basis of the analysis result, requesting second image data on the one or more target tissues, obtaining the second image data obtained by image-capturing the one or more target tissues, obtaining disease information on the plurality of disease indicators corresponding to the target tissue using a second artificial neural network, wherein the second artificial neural network is trained to obtain a target result value related to the plurality of disease indicators for the target tissue included in the image data, and providing a disease score on the basis of the target result value.

The technical solutions of the present disclosure are not limited to the above-described technical solutions and other technical solutions which are not described can be clearly understood by those skilled in the art to which the present disclosure pertains from the following description and the accompanying drawings.

BRIEF DESCRIPTION OF THE DRAWINGS

The above and other objects, features, and advantages of the present disclosure will become more apparent to those of ordinary skill in the art by describing exemplary embodiments thereof in detail with reference to the accompanying drawings, in which:

FIG. 7 is a view illustrating an image analysis operation performed in the server according to various embodiments;

FIG. 8 is a view illustrating an example of a disease score provided by the server, according to various embodiments;

DETAILED DESCRIPTION OF EXEMPLARY EMBODIMENTS

Figure 1:
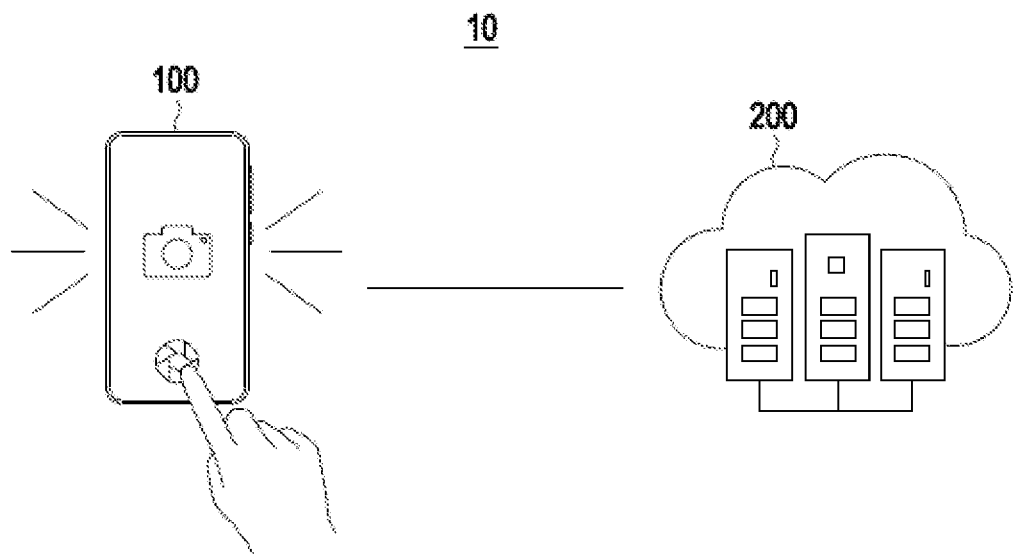
FIG. 1 is a view schematically illustrating a disease information providing system according to various embodiments.

The above and other objectives, features, and advantages of the present disclosure will become more apparent from the following description with reference to the accompanying drawings. However, the present disclosure may be modified into various forms and may have a variety of embodiments, and, therefore, specific embodiments will be illustrated in the drawings and described in detail below.

The embodiments described herein are intended to clearly describe the spirit of the present disclosure to those skilled in the art to which the present disclosure pertains, and thus the present disclosure is not limited to the embodiments described herein, and the scope of the present disclosure should be construed as including alternations or modifications without departing from the spirit of the present disclosure.

The drawings accompanying the present specification are provided to easily describe the present disclosure, and shapes shown in the drawings may be illustrated with exaggeration as necessary to help understanding of the present disclosure, and thus the present disclosure is not limited to the drawings.

When a detailed description of a known function or configuration related to the present disclosure is determined to unnecessarily obscure the gist of the present disclosure, the detailed description thereof will be omitted herein. In addition, numerical terms (e.g., "first," "second," and the like) used in the description of the present specification are merely detection symbols for distinguishing one component from another component.

In addition, suffixes "unit," "module," and "part" for components used in the following description are given or interchanged in consideration only of convenience of description, and thus these suffixes do not have distinctive meanings or functions.

The present specification relates to a disease information providing method using image analysis and a system for performing the same.

In the present specification, "disease information" has a comprehensive concept including determination of a characteristic or a state of an object to be analyzed, and second determination on the basis of the characteristic determination. In one embodiment, the disease information may include pathological information related to an object. For example, the disease information may include diagnostic information. The diagnostic information may be expressed as a probability value that an object is a disease tissue. In addition, the disease information may be provided as numerical information (e.g., a probability value) related to various disease indicators for an object.

Hereinafter, a disease information providing system 10 according to one embodiment of the present specification will be described with reference to FIGS. 1 and 2.

The diagnosis information providing system 10 according to one embodiment of the present specification is a system for providing disease information on an object by using image analysis.

FIG. 1 is a view schematically illustrating the disease information providing system according to various embodiments. FIG. 2 is a block diagram illustrating a general operation of the disease information providing system according to various embodiments.

Figure 2:
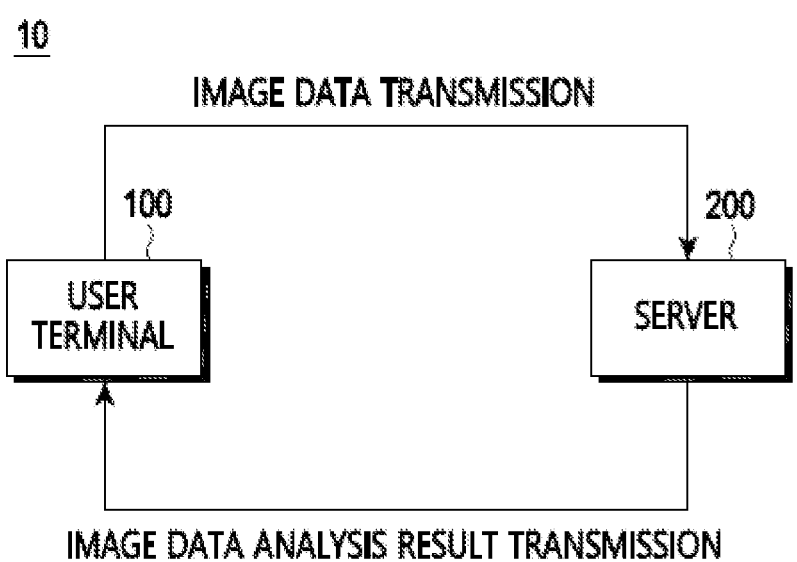
FIG. 2 is a block diagram illustrating a general operation of the disease information providing system according to various embodiments.

Referring to FIGS. 1 and 2, the disease information providing system 10 may include a user terminal 100 and an analysis server 200. The user terminal 100 and the analysis server 200 may be connected to each other through an online network.

According to various embodiments, the user terminal 100 may transmit data to the analysis server 200 and/or receive data from the analysis server 200. In one embodiment, the user terminal 100 may obtain image data necessary to provide disease information, and transmit the image data to the analysis server 200. For example, the user terminal 100 may transmit image data (or an image) obtained by capturing at least a part of the human body to the analysis server.

According to various embodiments, the analysis server 200 may receive image data from the user terminal 100 and analyze the received image data. In one embodiment, the analysis server 200 may analyze the image data using an artificial neural network model, detect a target included in the image data, and/or provide disease information on the target. Here, the term "target" may refer to a specific object included in the image data and targeted for obtaining disease information. For example, the target may be a skin tissue suspected of having a disease.

According to various embodiments, the disease information providing system 10 may provide disease information on a target, which is included in image data, by using the image data. In one embodiment, the disease information providing system 10 may obtain image data obtained by image-capturing at least a part of a body of a user (or another patient) through the user terminal 100, the analysis server 200 may analyze the obtained image data, and as a result, the disease information providing system 10 may provide disease information on the target included in the image data.

In the following description, the disease information providing system 10 for providing disease information related to a skin cancer is mainly described. That is, the disease information providing system 10 may analyze image data obtained by image-capturing an affected area suspected of a skin cancer, and provide disease information, which is related to the affected area, existing in the corresponding image data. However, the spirit of the present disclosure is not limited to the skin cancer, and may be applied to various diseases.

Figure 3:
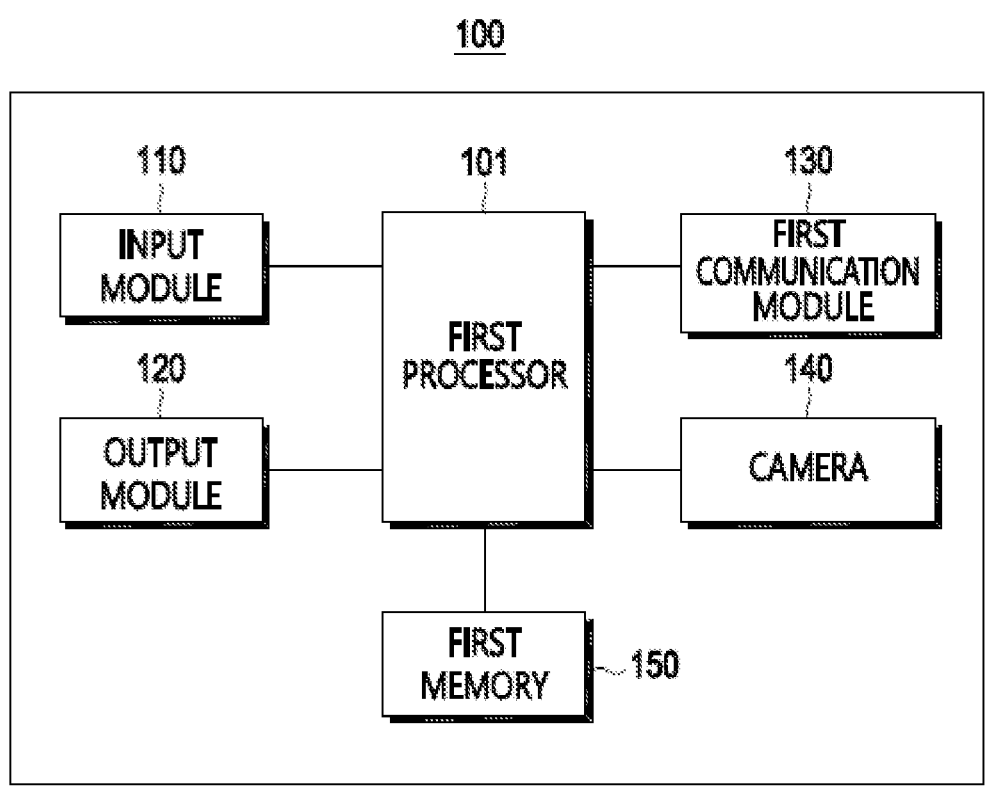
FIG. 3 is a block diagram illustrating a configuration of a user terminal according to various embodiments.

FIG. 3 is a block diagram illustrating a configuration of the user terminal according to various embodiments.

Referring to FIG. 3, the user terminal 100 may include all or some of a first processor 101, an input module 110, an output module 120, a first communication module 130, a camera 140, and a first memory 150. The user terminal 100 of FIG. 3 may have a configuration the same as or similar to that of the user terminal 100 of FIGS. 1 and 2, in whole or in part.

The first communication module 130 may perform communication with an external device. The user terminal 100 may transmit and receive data to and from the analysis server 200 or an external server through the first communication module 130. For example, the user terminal 100 may transmit image data to the analysis server 200 through the first communication module 130. For another example, the user terminal 100 may upload image data by accessing the Internet through the first communication module 130.

The first communication module 130 is broadly divided into a wired type module and a wireless type module. In some cases, the wired type module and the wireless type module may be simultaneously provided in the user terminal 100.

Here, in the case of the wired type module, a local area network (LAN) or a Universal Serial Bus (USB) communication is a typical example, and other methods are possible. In addition, in the case of the wireless type module, a wireless personal area network (WPAN)-based communication method such as Bluetooth or ZigBee may be mainly used. However, since a wireless communication protocol is not limited thereto, the wireless type communication module may use a wireless local area network (WLAN)-based communication method such as Wi-Fi or other known communication methods.

The first memory 150 may store various pieces of information. Various pieces of data may be temporarily or semi-permanently stored in the first memory 150. Examples of the first memory 150 may include a hard disk drive (HDD), a solid state drive (SSD), a flash memory, a read-only memory (ROM), a random access memory (RAM), and the like. The first memory 150 may be provided in the form embedded in the user terminal 100 or in the detachable from.

Various pieces of data required for an operation of the user terminal 100 in addition to an operating system (OS) for operating the user terminal 100 or a program for operating each component of the user terminal 100 may be stored in the first memory 150. For example, a program capable of processing an analysis result received from the analysis server 200 may be stored in the first memory 150.

The first processor 101 may control an overall operation of the user terminal 100. For example, the first processor 101 may load and execute a program for processing the image data analyzed by the analysis server 200 from the first memory 150, or provide an indication to a user through the output module 120.

The first processor 101 may be implemented as a central processing unit (CPU) or a device similar to the CPU according to hardware, software, or a combination thereof. The first processor 101 may be provided in the form of an electronic circuit for processing an electrical signal to perform a control function in hardware, and may be provided in the form of a program or code for driving a hardware circuit in software.

The user terminal 100 may have a separate power supply unit or receive power from the outside in a wired or wireless manner, and may have a separate switch configured to control the power supply unit.

The input module 110 may receive a user input from the user. The user input may be made in various forms such as a key input, a touch input, and a voice input. The input module 110 is a comprehensive concept including not only a keypad, a keyboard, and a mouse which have a traditional form as well as a touch sensor for detecting a touch of a user, but also various types of input parts for detecting or receiving various types of user inputs. In addition, the input module 110 may be implemented in the form of an input interface (a USB port, a PS/2 port, and the like) for connecting an external input device for receiving a user input to an electronic device instead of a device for detecting the user input by itself.

The output module 120 may output and provide various pieces of information to the user. The output module 120 is a comprehensive concept including a display for outputting an image, a speaker for outputting a sound, a haptic device for generating vibrations, and various types of output devices. In addition to the above description, the output module 120 may be implemented in the form of a port type output interface for connecting individual output devices to an electronic device.

The camera 140 may capture an image of a surrounding environment of the user terminal 100. The camera 140 may be controlled by the first processor 101, and may capture an image of at least a part of the body of the user and generate image data.

Figure 4:
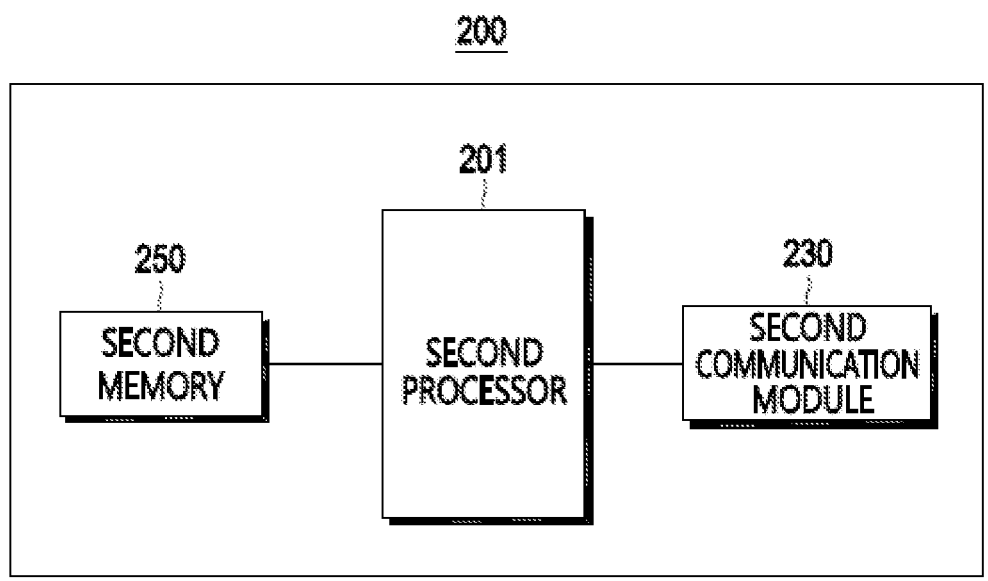
FIG. 4 is a block diagram illustrating a configuration of an analysis server according to various embodiments.

FIG. 4 is a block diagram illustrating a configuration of the analysis server according to various embodiments.

Referring to FIG. 4, the analysis server 200 may include all or some of a second processor 201, a second memory 250, and a second communication module 230. The analysis server 200 in FIG. 4 may mean the same configuration as the analysis server 200 in FIGS. 2 and 3 in whole or in part.

According to one embodiment of the present specification, the analysis server 200 may analyze the image data received from the user terminal 100 and provide disease information on a suspicious tissue included in the image data. The analysis server 200 may transmit the analysis result or disease information to the user terminal 100.

According to one embodiment of the present specification, the second processor 201 may obtain the image data, which is obtained by capturing a part of the body by the user terminal 100, using the second communication module 230, and determine pathological information on the suspicious tissue included in the image data using a program stored in the second memory 250.

The second communication module 230 may perform communication with an external device. The analysis server 200 may perform data communication with the user terminal 100 or an external server using the second communication module 230. For example, the analysis server 200 may obtain image data from the user terminal 100 using the second communication module 230.

The second communication module 230 may be provided similar to the first communication module 130, and thus a more detailed description thereof will be omitted.

The second memory 250 may store various pieces of information of the analysis server 200.

Various pieces of data required for an operation of the analysis server 200 in addition to an OS for driving the analysis server 200 or a program for operating each configuration of the analysis server 200 may be stored in the second memory 250. For example, a program for analyzing image data and an artificial neural network for data analysis may be stored in the second memory 250.

The second memory 250 may be provided similar to the first memory 150, and thus a more detailed description thereof will be omitted.

The second processor 201 may control an overall operation of the analysis server 200. For example, the second processor 201 may generate a control signal so as to load a program for processing and analyzing data from the second memory 250, process and analyze data obtained from the user terminal 100, and provide the result of the processing and analysis to the user through the user terminal 100.

The second processor 201 may be provided similar to the first processor 101, and thus a detailed description thereof will be omitted.

Hereinafter, a disease information providing method according to one embodiment of the present specification will be described. In the following description, the disease information providing method according to one embodiment of the present specification is described as being performed by the above-described disease information providing system 10. However, since this is only for convenience of description, the disease information providing method according to one embodiment of the present specification is not limited to being performed by the above-described disease information providing system 10. That is, the disease information providing method to be described below is not necessarily performed only by the disease information providing system 10 described above, and may be performed by another system or device having a function similar to that of the disease information providing system 10 described above.

Figure 5:
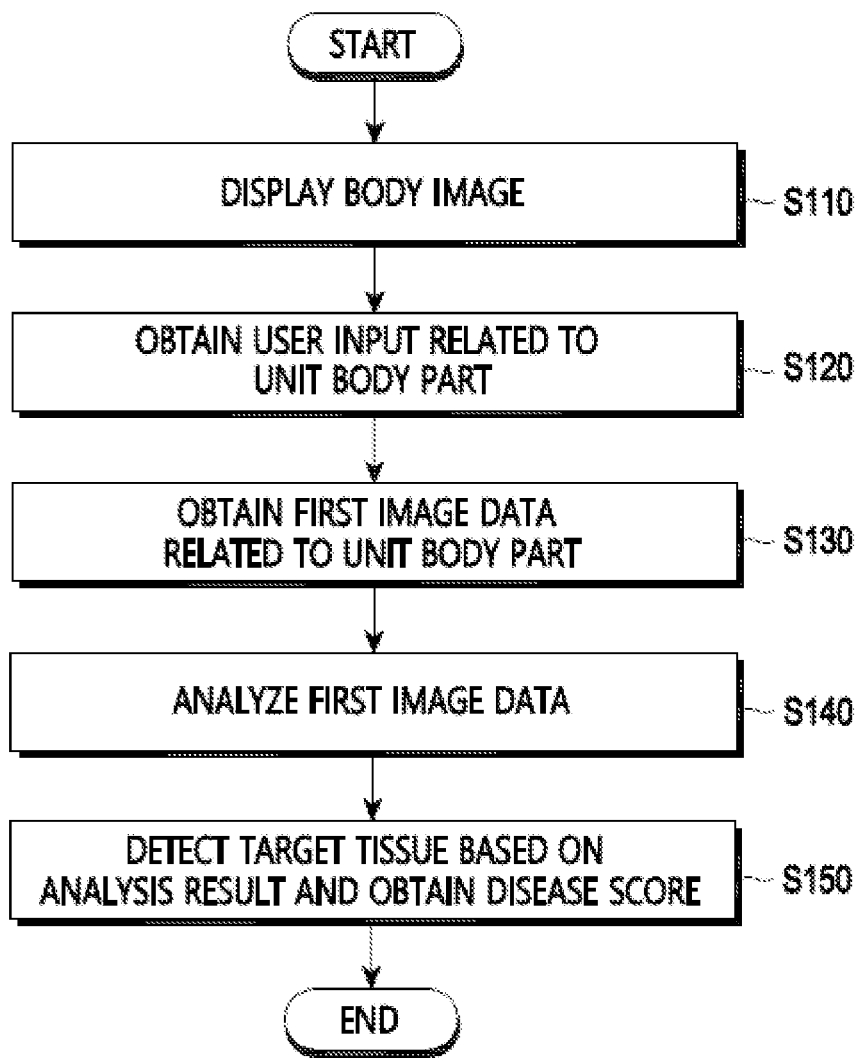
FIG. 5 is a flowchart illustrating a disease information providing method according to various embodiments.
Figure 6A:
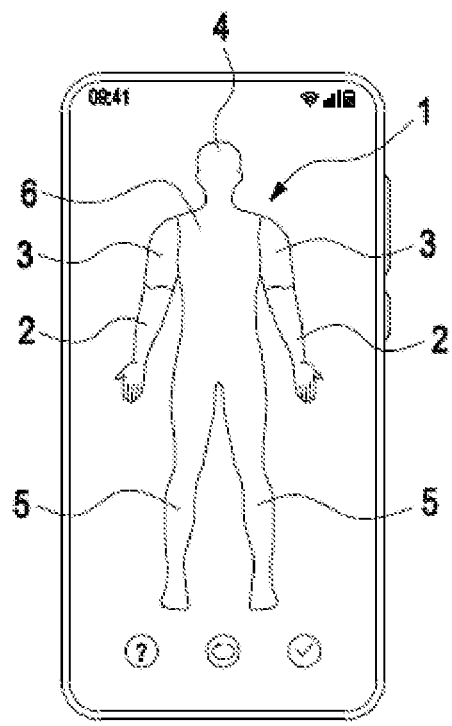
FIGS. 6A, 6B and 6C are views illustrating an operation in which disease information is provided by a user terminal, according to various embodiments.
Figure 6B:
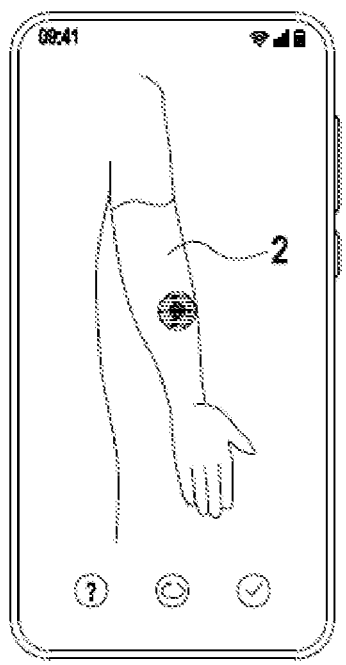
Figure 6C:
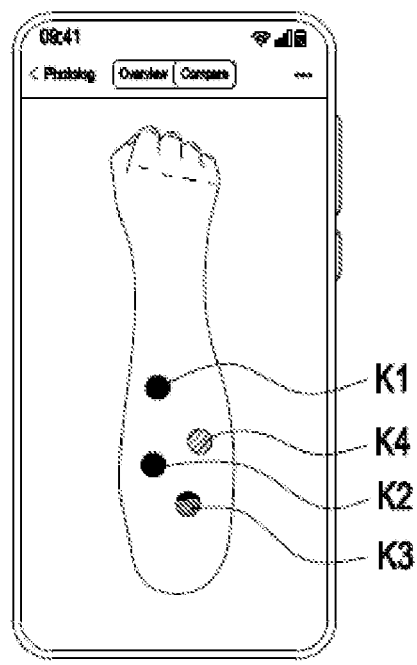

FIG. 5 is a flowchart illustrating the disease information providing method according to various embodiments.

Referring to FIG. 5, the disease information providing method according to various embodiments may include all or some of operations of displaying a body image (S110), obtaining a user input related to a unit body part (S120), obtaining first image data related to the unit body part (S130), analyzing the first image data (S140), and detecting a target tissue on the basis of the analysis result and obtaining a disease score (S150).

According to various embodiments, the user terminal 100 may display a body image (S110). For example, the user terminal 100 may display a body image including at least two body parts through the output module 120. Here, the body image may be a whole body image, but is not necessarily limited thereto. In one embodiment, the body image may be divided into a plurality of unit body parts.

According to various embodiments, the user terminal 100 may obtain a user input related to the unit body part (S120). For example, a user may select (e.g., applies a touch input to) at least one of the unit body parts, which are included in the displayed body image, related to a body part (e.g., a body part with skin tissues for which it is unclear whether or not a disease is present) for which the user wants to receive disease information.

According to various embodiments, the user terminal 100 may obtain first image data related to the selected unit body part (S130). Here, the first image data may mean image data obtained by image-capturing the entire unit body part. In addition, in the first image data, skin tissues in which it is unclear whether they are disease tissues may be image-captured together. In the following description, the skin tissues in which it is not clear whether they are disease tissues are referred to as "suspicious tissues."

According to various embodiments, the user terminal 100 may transmit the obtained first image data to the analysis server 200, and the analysis server 200 may analyze the first image data (S140). As will be described below, the analysis server 200 may analyze the first image data using an artificial neural network.

According to various embodiments, the analysis server 200 may transmit the analysis result of the first image data to the user terminal 100, and the user terminal 100 may detect a target tissue and obtain a disease score.

The functions related to the artificial neural network model used in the present disclosure are operated through a processor (e.g., the second processor 201) and a memory (e.g., the second memory 250). The second processor 201 may be composed of one or a plurality of processors. In this case, the one or more processors may include a general purpose processor such as a CPU, an application processor (AP), a digital signal processor (DSP), or the like, a graphics dedicated processor such as a graphics processing unit (GPU), a vision processing unit (VPU), or an artificial neural network dedicated processor such as a neural processing unit (NPU). The one or more processors control to process input data according to a predefined operation rule or an artificial neural network model stored in the second memory 250. Alternatively, when the one or more processors include an artificial neural network dedicated processor, the artificial neural network dedicated processor may be designed with a hardware structure specialized for processing a specific artificial neural network model.

The artificial neural network model may be implemented in the form of a classifier for generating diagnosis assistance information. The classifier may perform binary classification or multi-class classification. For example, the neural network model may be a binary classification model that classifies input data into a normal or abnormal class with respect to target diagnosis assistance information such as a specific disease or an abnormal symptom. Alternatively, the neural network model may be a multi-class classification model that classifies the input data into a plurality of rating classes with respect to a specific characteristic (e.g., a degree of disease progression). Alternatively, the neural network model may be implemented as a regression model for outputting a specific value related to a specific disease.

The predefined operation rule or artificial neural network model is characterized by being made through learning. Here, being made through learning may means that a basic artificial neural network model is trained using a plurality of pieces of learning data by a learning algorithm, thereby creating a predefined operation rule or artificial neural network model set to perform a desired characteristic (or purpose). Such learning may be performed by a device itself in which an artificial neural network according to the present disclosure is performed, or may be made through a separate server and/or system. Examples of the learning algorithm include supervised learning, unsupervised learning, semi-supervised learning, or reinforcement learning, but the learning algorithm is not limited to the above examples The artificial neural network model may be made through learning. The artificial neural network model may be composed of a plurality of neural network layers. Each of the plurality of neural network layers may have a plurality of weight values, and may perform a neural network calculation through calculations between a calculation result of a previous layer and a plurality of weight values. The plurality of weight values that the plurality of neural network layers may be optimized by learning results of the artificial neural network model. For example, the plurality of weight values may be updated to reduce or minimize a loss value or a cost value obtained from the artificial neural network model during the learning process.

The artificial neural network may include a deep neural network (DNN), for example, a convolutional neural network (CNN), a deep neural network (DNN), a recurrent neural network (RNN), a generative adversarial network (GAN), a restricted boltzmann machine (RBM), deep belief network (DBN), bidirectional recurrent deep neural network (BRDNN), deep Q-networks, and the like, but the artificial neural network is not limited to the above examples.

Hereinafter, an implementation of the disease information providing method of FIG. 5 will be described with reference to FIGS. 6 to 10.

FIG. 6 is a view illustrating an operation in which disease information is provided by the user terminal, according to various embodiments.

Referring to FIG. 6, the user terminal 100 may obtain image data obtained by image-capturing at least a part of the body.

According to various embodiments (mainly referring to FIG. 6A), the user terminal 100 may display an image 1 related to the body. Specifically, the first processor 101 may display the body image 1 through the output module 120. Here, the body image 1 may be a whole body image or an image of a part of the body.

According to various embodiments, the user terminal 100 may obtain a user input for unit body parts 2 to 6 from a user. Here, the unit body parts 2 to 6 may mean body parts for which disease information is to be provided. In addition, the unit body parts 2 to 6 may mean at least some of the body which may be physically divided. In addition, the unit body parts may be distinguished in various ways.

As an example, the unit body parts may be divided into at least some of a hand, an arm 2, a shoulder 3, a chest 6, an abdomen, a back, a leg 5, an arm, and a head 4. In addition, the hand may be further subdivided into fingers, and the arm may be further subdivided into upper and lower arms.

According to various embodiments, the user may select at least one of at least some unit body parts 2 to 6 included in the body image output through the output module 120. For example, the user may select the unit body part, for which the user wants to receive disease information, from the displayed body image through an input module (e.g., a touch input).

In some embodiments, the body image 1 output through the user terminal 100 may be adjusted in composition. In one embodiment, the body included in the body image 1 may be rotated, enlarged/reduced, and/or moved. The user may select optimal unit body parts 2 to 6 while adjusting the composition of the body image 1.

According to various embodiments (referring to FIG. 6B), the user terminal 100 may provide an indication requesting upload of an image related to the unit body part 2 in response to the user input. In one embodiment, the user terminal 100 may display an image related to the unit body part (e.g., the arm 2) corresponding to the user input, and display the indication requesting upload of the image for the corresponding unit body part 2 together.

According to various embodiments (mainly referring to FIG. 6C), the user terminal 100 may obtain first image data related to the unit body part from the user. For example, the user may upload a photograph related to the selected unit body part or first image data obtained by image-capturing the selected unit body part. In some embodiments, the user terminal 100 may drive the camera 140 in response to the user input to allow the user to image-capture, in real time, the unit body part.

In some embodiments, the user terminal 100 may compare the uploaded first image data with the unit body part selected by the user input. For example, when the user selects the arm as the unit body part and uploads image data related to the leg, the first processor 101 may analyze whether the uploaded image data corresponds to the arm. As a result of the analysis, when the uploaded image data does not correspond to the arm, the user terminal 100 may provide an indication related to requesting the user to upload another photograph or the occurrence of an error.

In some embodiments, the body image 1 may not be divided into the plurality of unit body parts 2 to 6. For example, since a suspicious tissue may be located at a position that is difficult to be clearly distinguished, such as a boundary between an arm and a shoulder, the user may upload the first image data without separately selecting the unit body parts 2 to 6. In addition, in some embodiments, the user may select a body part, in which a suspicious tissue is generated, from the body image 1 itself that is not divided into the plurality of unit body parts 2 to 6, and upload first image data related to the corresponding part. That is, the division of the body image 1 into the unit body parts 2 to 6 may not be performed.

FIG. 7 is a view illustrating an image analysis operation performed in the server according to various embodiments. FIG. 8 is a view illustrating an example of a disease score provided by the server, according to various embodiments.

Referring to FIGS. 7 and 8, the analysis server 200 may obtain a disease score from image data using a previously trained artificial neural network model. In the description of the present disclosure, the artificial neural network model may be mainly for detecting an object from image data, but the present disclosure is not limited thereto. For example, models such as a regional convolutional neural network (RCNN), a Fast-RCNN, a Faster-RCNN, a Fastest-RCNN, and You Only Look Once (YOLO) may be used as the artificial neural network model.

According to various embodiments, an artificial neural network model 202 may be trained with a learning data set in which pieces of previously obtained image data are tagged with a disease indicator. In one embodiment, the disease indicator may be divided into two or more types of indicators. For example, the disease indicator may include a malignant indicator, a pre-malignant indicator, and a benign indicator. In one embodiment, the disease indicator may be divided again into detailed disease indicators. For example, the malignant disease indicator may be subdivided into malignant melanoma, basal cell cancer, and squamous-cell cancer. For another example, the pre-malignant disease indicator may be subdivided into actinic keratosis, atypical nevus syndrome, and giant pigmented nevus. For still another example, the benign disease indicator may be subdivided into all or some of anepidermal cyst, wart, seborrheic keratosis, milium, sebaceous hyperplasia, dermatofibroma, a mole, a corn, callus, and/or a freckle.

According to various embodiments, the sufficiently trained artificial neural network may analyze the image data and obtain a disease score of a tissue included in the image data.

In one embodiment, the disease score may be generated by combining result values of the artificial neural network model for a plurality of disease indicators assigned to suspicious tissues included in the image data. Alternatively, the disease score may mean a result value (or each value derived therefrom) of the artificial neural network model for each of the plurality of disease indicators assigned to the tissue included in the image data. Here, the result value of the artificial neural network model may mean a probability value that a suspicious tissue included in the first image data corresponds to one of the plurality of disease indicators. For another example, the result value of the artificial neural network model may also mean a result value. Hereinafter, the "result value of the artificial neural network model" is abbreviated and simply referred to as a "result value."

According to various embodiments, the disease score may be divided into a plurality of different scores. In one embodiment, the disease score may include at least one of a detailed score, a type score, and a total score.

In one embodiment, the detailed score may be a result value of the artificial neural network model for a plurality of detailed disease indicators. For example, the detailed score may mean a probability value that the result value corresponds to the plurality of detailed disease indicators. In this case, the sum of the detailed scores may be 1.

According to various embodiments, a total score T may be generated on the basis of all or some of detailed scores M1 to M3, P1 to P3, and B1 to B10. In one embodiment, the total score T may be generated on the basis of a value obtained by assigning a weight value to all or some of the detailed scores M1 to M3, P1 to P3, and B1 to B10. For example, the total score T may be generated on the basis of a value obtained by assigning a weight value to the detailed scores M1 to M3 related to the malignant disease indicators and/or the detailed scores P1 to P3 related to the pre-malignant disease indicators. In this case, as an example, a weight value greater than that assigned to the detailed scores P1 to P3 related to the pre-malignant disease indicators and/or the detailed scores B1 to B10 related to the benign disease indicators may be assigned to the detailed scores M1 to M3 related to the malignant disease indicators. In addition, a weight value greater than that assigned to the detailed scores B1 to B3 related to the benign disease indicators may be assigned to the detailed scores P1 to P3 related to the pre-malignant disease indicators. In one embodiment, in calculating the total score T, only the detailed scores M1 to M3 related to the malignant disease indicators and the detailed scores P1 to P3 related to the pre-malignant disease indicators may be used. In this case, a weight value greater than 0 and less than 1 may be assigned to the detailed scores P1 to P3 related to the pre-malignant disease indicators.

In some embodiments, the type score for the malignant disease indicator may be expressed as "Mt1." Here, the type score may be generated by combining result values for the detailed indicators included in the same disease indicator. For example, the type score Mt1 for the malignant disease indicator may be generated by combining the detailed scores M1, M2, and M3 for the detailed disease indicators. As an example, the type score Mt1 may be an average value of the detailed scores M1, M2, and M3. As another example, the type score Mt1 may be the highest or lowest value among the detailed scores M1, M2, and M3. As still another example, the type score Mt1 may be a median value of the detailed scores M1, M2, and M3. In some embodiments, the type score Mt1 may be generated on the basis of a weight value assigned to all or some of the detailed scores M1, M2, and M3. The description of the malignant disease indicator may be applied to the pre-malignant disease indicator and the benign disease indicator. The descriptions of the detailed scores M1, M2, and M3 and the type score Mt1 for the malignant disease indicators may be correspondingly applied to the detailed scores P1, P2, and P3 and a type score Pt1 for the pre-malignant disease indicators. Similarly, the descriptions of the detailed scores M1, M2, and M3 and the type score Mt1 for the malignant disease indicators may be correspondingly applied to the detailed scores B1, B2, B3, . . . , and B10 and a type score Bt1 for the benign disease indicators.

In one embodiment, the total score T may be generated by combining values of a plurality of type scores Mt1, Pt1, and Bt1. As an example, the total score T may be an average value of the type scores Mt1, Pt1, and Bt1. As another example, the total score T may be the highest or lowest value among the type scores Mt1, Pt1, and Bt1. As still another example, the total score T may be a median value of the type scores Mt1, Pt1, and Bt1.

Figure 9:
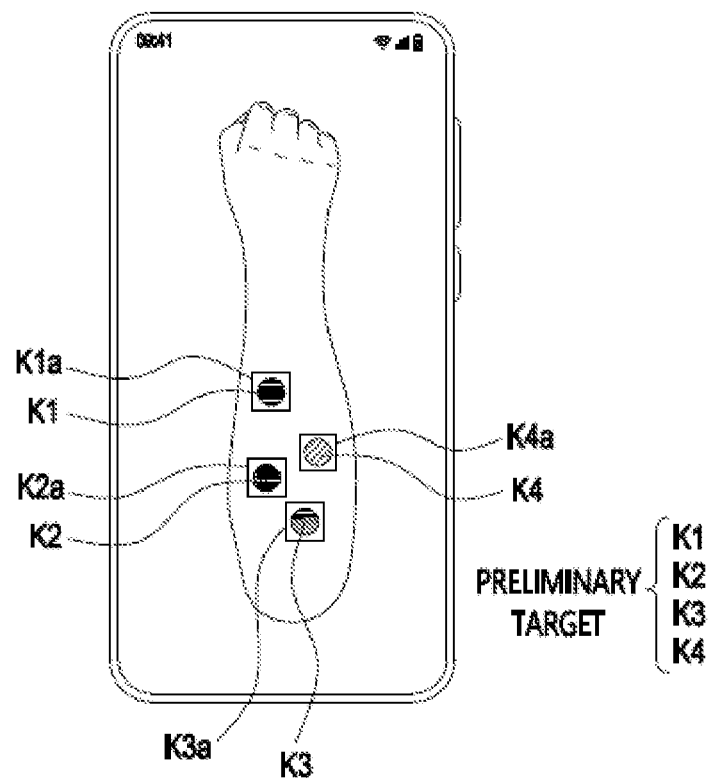
FIG. 9 is a view illustrating that detection of image data is performed, according to various embodiments.
Figure 10:
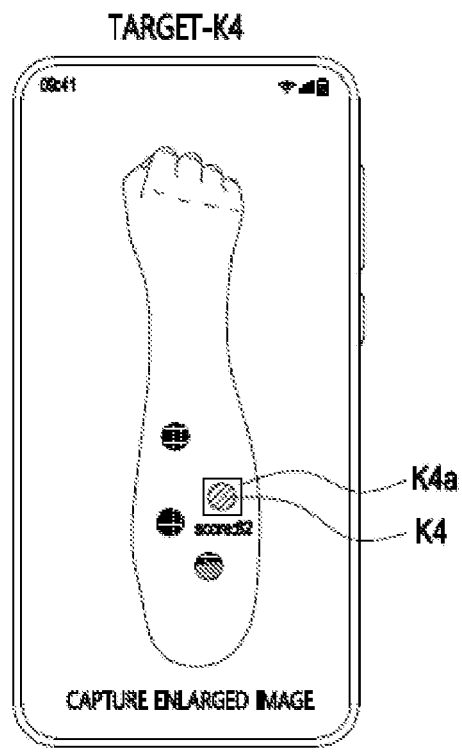
FIG. 10 is a view illustrating that a target tissue is detected from the image data, according to various embodiments.

FIG. 9 is a view illustrating that detection of a suspicious tissue in image data is performed, according to various embodiments. FIG. 10 is a view illustrating that a target tissue is detected from the image data, according to various embodiments.

Referring to FIGS. 9 and 10, the disease information providing system 10 may analyze the first image data to detect at least one suspicious tissue included in the first image data. In describing FIGS. 9 and 10, reference may be made to FIG. 8.

According to various embodiments, the analysis server 200 may detect one or more suspicious tissues included in the first image data. In some embodiments, the user terminal 100 may divide and display the detected suspicious tissues. In the following description, suspicious tissues (e.g., bounding box regions detected in the image data), which are detected from the image data as a result of the analysis by the analysis server 200, will be referred to as "preliminary target tissues."

According to various embodiments, the disease score may be used when the analysis server 200 detects the preliminary target tissues. In one embodiment, a partial region in the first image data whose disease score is confirmed to be greater than or equal to a threshold value may be detected as the preliminary target tissue. Here, the disease score may use at least one of the above-described detailed score, type score, and/or total score. In addition, here, the disease score for detecting the preliminary target tissue in the image data may be referred to as a "detection score." Thus, in the present disclosure, the terms "disease score" and "detection score" may be interchangeably used. In some embodiments, the detection score may be derived by a result value related to the malignant disease indicator and/or the pre-malignant disease indicator associated with a disease. In another embodiment, in order to detect a skin tissue that is specific in shape, the detection score may be derived by a result value for the benign disease indicator. Thus, when the detection score is less than the threshold value, the analysis result of the analysis server 200 may not be detected as the preliminary target tissue even when the detection score is an abnormal tissue when viewed with the naked eye.

In various embodiments, the threshold value may be determined in consideration of a degree of relevance to a disease. For example, as the threshold value is set to be large, tissues having greater relevance to a disease may be detected. In contrast, as the threshold value is set to be small, tissues that are less relevant to a disease may be detected. In some embodiments, the threshold value may be set by a user. In addition, the threshold value may be determined on the basis of the type of the disease indicator used to generate the detection score. For example, when the detection score is generated only by using the malignant disease indicator and/or the pre-malignant disease indicator, tissues associated with a disease may be detected even when the threshold value is set to be relatively low.

According to various embodiments, the analysis server 200 may detect at least one target tissue included in the first image data. In one embodiment, the target tissue is a tissue suspected to be a disease, and may refer to a tissue in which detailed pathological information is required. For example, the target tissue may be detected in the first image data by a detection score derived from a combination of all or some of the disease scores for the malignant disease indicators and/or the disease scores for the pre-malignant disease indicators. In addition, in some embodiments, among the preliminary target tissues whose detection scores are confirmed to be greater than or equal to a threshold value, specific suspicious tissues whose detection scores are confirmed to be greater than or equal to a higher threshold value may be considered as target tissues. Here, the threshold value for detecting the preliminary target tissue may be referred to as a first threshold value, and the threshold value for detecting the target tissue may be referred to as a second threshold value.

Referring to FIGS. 9 and 10 together, the analysis server 200 may classify various preliminary target tissues included in the first image data (see FIG. 9), and may further detect the target tissue having greater relevance to a disease from among the classified suspicious tissues (see FIG. 10). According to some embodiments, the analysis server 200 may provide only the result value for the disease indicator of pixels included in the first image data, and the first processor 101 of the user terminal 100 may detect the suspicious tissues and/or the target tissue.

In some embodiments, the analysis server 200 may detect only the target tissue. For example, in a specific case, since the user wants to have only information on a tissue related to a disease, the analysis server 200 may detect only a target tissue having a relatively high degree of relevance to the disease.

According to various embodiments, the system 10 may divide and display the preliminary target tissue and/or the target tissue, and simultaneously tag and display the preliminary target tissue and/or the target tissue with disease information related to the preliminary target tissue and/or the target tissue. In one embodiment, the user terminal 100 may display a bounding box for dividing the preliminary target tissue and/or the target tissue together with the disease score corresponding to the bounding box. A method of tagging disease information in the user terminal 100 may be variously used. For example, the user terminal 100 may tag the disease information so as to be located adjacent to the preliminary target tissue and/or the target tissue. For another example, when a user input for the preliminary target tissue and/or the target tissue is received (e.g., a user applies a touch input), the user terminal 100 may display the disease information. Alternatively, the analysis server 200 may transmit information to be displayed through the user terminal 100. In addition, various implementation modifications are possible.

According to various embodiments, the user terminal 100 may display the preliminary target tissue and the target tissue to be distinguished from each other. According to one embodiment, the user terminal 100 may provide different indications for the preliminary target tissue and the target tissue. For example, the user terminal 100 may display the preliminary target tissue and the target tissue to be distinguished by different colors. For another example, the preliminary target tissue and the target tissue may be distinguished by different sizes. The analysis server 200 may transmit information to be displayed through the user terminal 100. In addition, various implementation modifications are possible.

In some embodiments, the user terminal 100 may provide different indications on the basis of the disease score (or the detection score) confirmed in the corresponding preliminary target tissue and/or target tissue. In one embodiment, as the disease score is higher, a visually stimulating indication may be provided. For example, as the disease score is higher, the indication of dark color may be provided, or as the disease score is lower, the indication of light color may be provided. Here, the indication may be applied to the bounding box and/or pixels in the first image data. For example, when first to third preliminary targets K1, K2, and K3 have disease scores greater than or equal to the first threshold value described above, and a fourth target K4 has a disease score greater than or equal to the second threshold value, indications (e.g., bounding boxes K1a, K2a, and K3a) for the first to third preliminary targets K1, K2, and K3 and an indication (e.g., a bounding box K4a) for the fourth target K4 may be visually distinguished. For example, the bounding boxes may be expressed by different colors.

According to various embodiments, the analysis server 200 may determine position information of the preliminary target tissue. In one embodiment, the analysis server 200 may detect, as a preliminary target tissue region, a set of pixels in which result values for the disease indicators are greater than or equal to a threshold value, and determine position information on the preliminary target tissue region. Here, the position information on the preliminary target tissue region may be determined on the basis of position of the bounding box or the pixels in the image data. According to various embodiments, the user terminal 100 may provide the position information of the preliminary target tissue and/or the target tissue to the user.

In some embodiments (referring to FIG. 10), the system 10 may visually divide only the target tissue K4 having a high disease score (high degree of relevance to a disease). For example, when a threshold value related to a disease is 80, the analysis server 200 may divide only the target K4 having a disease score of 80 or more with a bounding box. The user terminal 100 may receive and display corresponding information.

According to various embodiments, the system 10 may request re-capturing for the target tissue K4 having a high disease score. However, as shown in FIG. 9, the re-capturing may also be requested for the preliminary target tissues K1, K2, and K3. That is, a third threshold value for the disease score may be set, and the re-capturing may be requested for the preliminary targets and/or the target tissues whose disease scores are greater than or equal to the third threshold value. Here, the third threshold value may be a threshold value of the disease score for which the re-capturing is required. In one embodiment, when the disease score is greater than or equal to the second threshold value (e.g., high degree of relevance to a disease), the analysis server 200 may request to capture second image data on the target tissue K4. The user terminal 100 may display a request for capturing the second image data so that the user recognizes the request. Here, the second image data may be an enlarged image of the target tissue K4. For example, the second image data may be a proximity image or a dermascopic image of the target tissue K4, but the present disclosure is not limited thereto.

Figure 11:
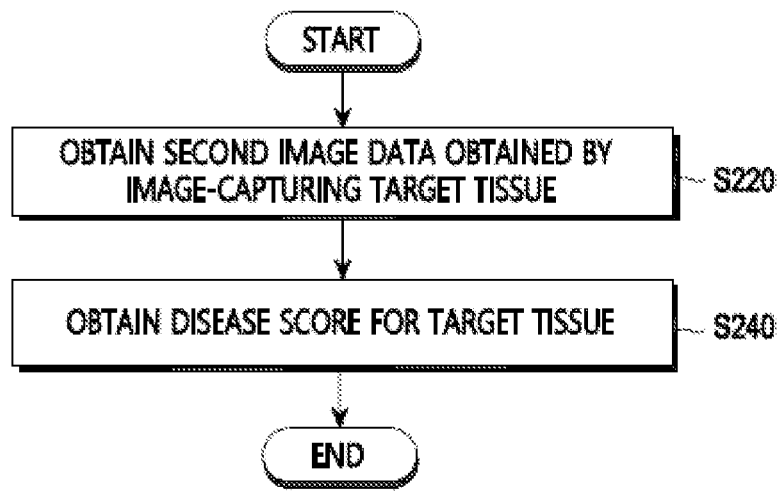
FIG. 11 is a flowchart illustrating a method of providing disease information related to a target tissue, according to various embodiments.

FIG. 11 is a flowchart illustrating a method of providing disease information related to a target tissue, according to various embodiments.

Referring to FIG. 11, the method of providing disease information related to a target tissue may include obtaining second image data obtained by image-capturing a target tissue (S220), and obtaining a disease score for the target tissue (S240).

According to various embodiments, the system 10 may obtain second image data obtained by image-capturing the target tissue (S220). Here, the second image data is image data obtained by image-capturing a tissue that is detected as the target tissue (or a preliminary target tissue) in the first image data, and may mean image data obtained by enlarging and image-capturing the corresponding target tissue. The user terminal 100 may transmit the second image data to the analysis server 200.

In various embodiments, the system 10 may provide an indication requesting to upload the second image data on the target tissue. For example, the user may select (e.g., apply a touch input to) at least one target tissue (or preliminary target tissue) among target tissues (or preliminary target tissues) detected as a result of analysis of the first image data, and the user terminal 100 may request to upload the second image data on the selected target tissue.

According to various embodiments, the analysis server 200 may analyze the second image data and provide a disease score for the target tissue included in the second image data (S240). Specifically, the analysis server 200 may provide the disease score for the target tissue included in the second image data.

Figure 12:
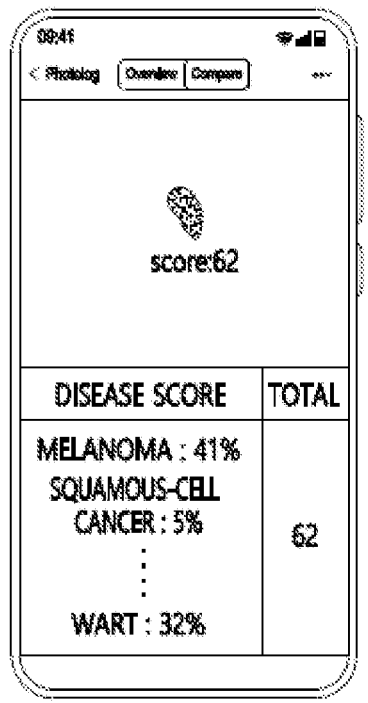
FIG. 12 is a view illustrating a state in which disease information on a target tissue is provided, according to various embodiments.

FIG. 12 is a view illustrating a state in which disease information on a target tissue is provided, according to various embodiments.

Referring to FIG. 12, the system 10 may provide disease information on the target tissue included in the second image data. Here, the second image data may be an enlarged image or a dermascopic image, as described above.

According to various embodiments, the system 10 may provide disease information on the target tissue detected from the second image data. For example, the detected information on the target tissue may be provided together with a disease score. Here, all of the detailed scores for the detailed disease indicator described above may be provided as the disease score. Of course, a weight value may be applied to the detailed score according to the disease indicator. In addition, result values related to the target tissue (or the preliminary target tissue) may be referred to as a target result value.

According to various embodiments, the analysis server 200 may detect the target tissue in the second image data on the basis of position information of the target tissue (or the preliminary target tissue). For example, the analysis server 200 may provide disease information on the target tissues corresponding to each other by comparing the position information of the target tissue detected in the first image data with the position information of the target tissue detected in the second image data.

According to various embodiments, when the user selects (e.g., applies a touch input to) the target tissue output from the user terminal 100, disease information on the corresponding target tissue may be provided. For example, in a case in which two or more target tissues exist in the second image data, when the user applies a touch input to one target tissue, the user terminal 100 may provide disease information on the corresponding target tissue. In some embodiments, when two or more target tissues exist in the second image data, the user terminal 100 may provide comparison information on each of the target tissues.

Figure 13:
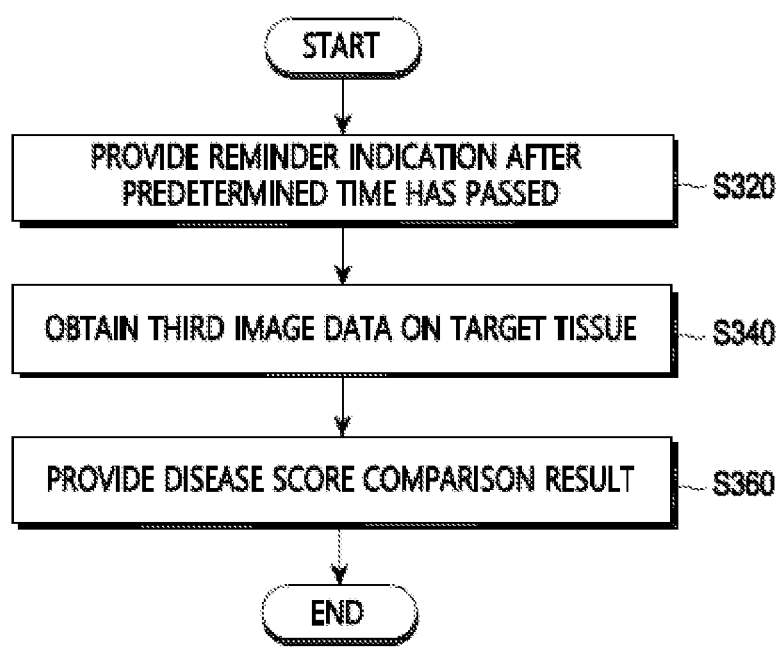
FIG. 13 is a flowchart illustrating a disease information providing method including a reminder indication, according to various embodiments.

FIG. 13 is a flowchart illustrating a disease information providing method including a reminder indication, according to various embodiments.

Referring to FIG. 13, the disease information providing method including a reminder indication may include providing a reminder indication after a predetermined time has passed (S320), obtaining third image data on the target tissue (S340), and providing a disease score comparison result (S360).

Figure 14A:
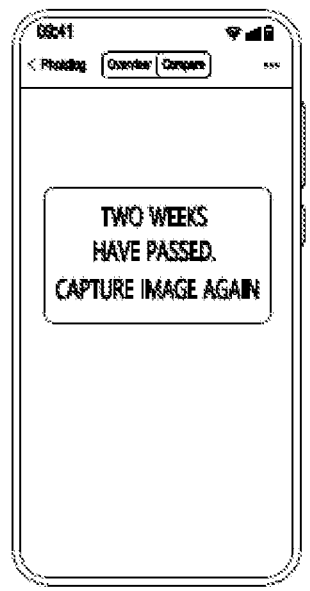
FIGS. 14A, 14B and 14C are views illustrating a state in which the disease information providing method of FIG. 13 is implemented.

According to various embodiments (referring to FIG. 14A), when a predetermined time has passed after the analysis result for the first image data or the analysis result for the second image data is provided, the system 10 may provide a reminder indication to the user. The reminder indication may be provided by the analysis server 200 or the user terminal 100. For example, after a predetermined period has passed, the analysis server 200 may transmit a signal for providing the reminder indication to the user terminal 100, and the user terminal 100 may provide the reminder indication in response thereto. Here, the predetermined time may mean a period in which re-diagnosis of a tissue suspected of a disease is required. For example, the predetermined time may be two weeks. Here, the predetermined time may be determined on the basis of the disease score of the corresponding target tissue (or the preliminary target tissue). For example, when the disease score of the target tissue (or the preliminary target tissue) is low, the reminder indication may be provided after a relatively longer time than in a case in which the disease score is high. According to one embodiment, the reminder indication may be provided through the output module 120 of the user terminal 100. The reminder indication may be provided as visual information through a display, tactile information through vibration, and/or sound information. In addition, various methods may be used.

According to various embodiments, the user terminal 100 may obtain third image data related to the target tissue K4. Here, the third image data may be image data captured at a composition substantially the same as or similar to that of the above-described first image data or second image data. Alternatively, the third image data may mean image data obtained by image-capturing the target tissue K4 (or the preliminary target tissues K1, K2, and K3) included in the first image data or the second image data. The user terminal 100 may transmit the third image data to the analysis server 200.

According to various embodiments, the analysis server 200 may provide a disease score comparison result. In one embodiment, the analysis server 200 may analyze the third image data, detect the preliminary target tissue and/or the target tissue included in the third image data, and obtain the disease score. After the analysis of the third image data, the analysis server 200 may compare disease scores for a target tissue K4' and a preliminary target tissue included in the first image data and disease scores for a target tissue K4" and a preliminary target tissue, which are included in the third image data, corresponding to the target tissue K4' and the preliminary target tissue included in the first image data. Similarly, the disease scores of the second image data and the third image data may be compared.

Figure 14B:
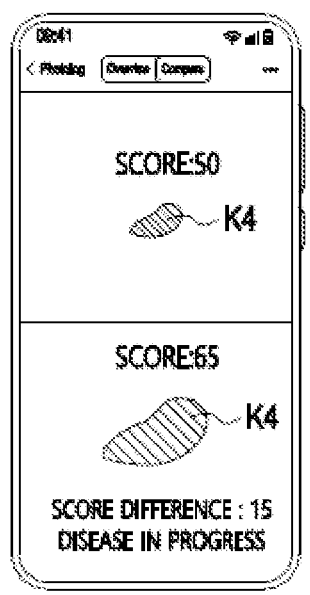
Figure 14C:
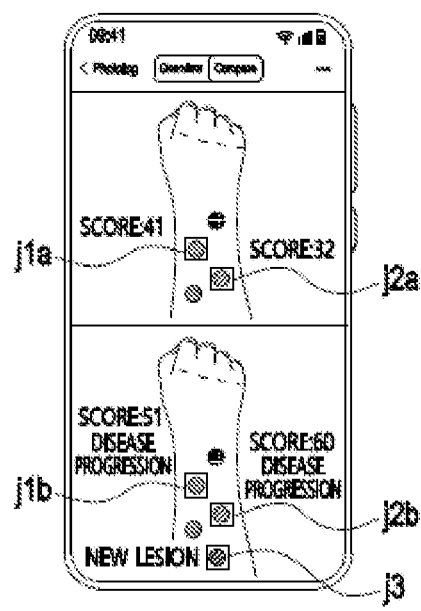

FIG. 14 is a view illustrating a state in which the disease information providing method of FIG. 13 is implemented.

Referring to FIG. 14, the system 10 may provide a disease score comparison result of the first image data (and/or the second image data) and the third image data.

According to various embodiments, after the analysis of the third image data, the analysis server 200 may compare the disease scores for the target tissue K4' and the preliminary target tissue included in the first image data and the disease scores for the target tissue K4" and the preliminary target tissue, which are included in the third image data, corresponding to the target tissue K4' and the preliminary target tissue included in the first image data. Similarly, the disease scores of the second image data and the third image data may be compared.

According to various embodiments, the system 10 may compare the disease score of the target tissue K4' included in the first image data with the disease score of the target tissue K4" included in the third image data, and output a result of the comparison. For example, the user terminal 100 may output the disease score and/or a difference value (e.g., a difference value of 15 in FIG. 14B) of each of the target tissues K4' and K4" respectively included the first image data and the third image data and corresponding to each other. Here, in determining the target tissues corresponding to each other, the above-described position information may be substantially used.

In one embodiment, when the difference between the disease score value of the target tissue included in the first image data and the disease score value of the target tissue included in the third image data is greater than or equal to a fourth threshold value, the user terminal 100 may provide a first alarm to the user. For example, the fourth threshold value may mean a threshold value for a disease score difference value for generating an alarm. In addition, the alarm may mean that the target tissue is associated with a disease or may reflect that the target tissue has grown significantly. As another example, when the difference between the disease score value of the target tissue included in the first image data and the disease score value of the target tissue included in the third image data is insignificant or is less than a fifth threshold value, the user terminal 100 may provide a second alarm to the user. Here, the second alarm may mean that the target tissue (or the preliminary target tissue) is less associated with a disease or may reflect that the target tissue does not significantly grow.

According to various embodiments, the system 10 may compare the first image data (or the second image data) with the third image data to determine whether a new lesion occurs. In one embodiment, the analysis server 200 may determine a degree of disease progression between the target tissue (or preliminary target tissues J1a and J2a) in the first image data and the target tissue (or preliminary target tissues J1b and J2b) in the third image data, and may determine whether a new suspicious tissue J3 has occurred. The analysis server 200 may divide the new suspicious tissue J3, and the user terminal 100 may divide and display the new suspicious tissue J3.

The disease information providing methods described above may be performed only by the user terminal 100 or the analysis server 200, or at least some of which may be performed by the user terminal 100 and at least some of which may be performed by the analysis server 200. In some embodiments, the system 10 may be integrated into one device.

According to various embodiments, provided is a disease information providing method performed by an analysis server including a memory and a processor configured to drive a program loaded from the memory, the method including obtaining first image data obtained by image-capturing a body part and one and more suspicious tissues located in the body part, analyzing the first image data using an artificial neural network, wherein the first artificial neural network is trained to detect a target tissue related to a disease from the image data obtained by image-capturing the body part, detecting one and more target tissues, in which a detection score derived from a result value of at least some of a plurality of disease indicators is analyzed to be greater than or equal to a threshold value, from among the one and more suspicious tissues included in the first image data on the basis of the analysis result, requesting second image data on the one and more target tissues, obtaining the second image data obtained by image-capturing the one and more target tissues, obtaining disease information on the plurality of disease indicators corresponding to the target tissue using a second artificial neural network, wherein the second artificial neural network is trained to obtain a target result value related to the plurality of disease indicators for the target tissue included in the image data, and providing a disease score on the basis of the target result value.

According to one embodiment, the plurality of disease indicators may include at least some of a malignant disease indicator, a benign disease indicator, and a pre-malignant disease indicator.

According to one embodiment, the malignant disease indicator may include indicators each reflecting three or more diseases, the benign disease indicator may include indicators each reflecting five or more benign tissues, and the pre-malignant disease indicator may include indicators each reflecting two or more preliminary diseases.

According to one embodiment, the disease score may be generated by combining at least some of a target result value for the malignant disease indicator, a target result value for the pre-malignant disease indicator, and a target result value for the benign disease indicator.

According to one embodiment, the disease score may be generated by combining a value obtained by assigning a weight value to the target result value for the malignant disease indicator with a value obtained by assigning a weight value to the target result value for the pre-malignant disease indicator, and the weight value may be selected in a range of more than 0 and less than or equal to 1.

According to one embodiment, the detection score may be generated by combining a result value for the malignant disease indicator and a result value for the pre-malignant disease indicator.

According to one embodiment, the threshold value may include a first threshold value and a second threshold value greater than the first threshold value, and the method further include instructing to provide different indications in a case in which the detection score is greater than or equal to the first threshold value and less than the second threshold value and in a case in which the detection score is greater than or equal to the second threshold value.

According to one embodiment, the disease score may include disease information on three indicators having the largest value among the plurality of target result values.

According to one embodiment, the disease information providing method may further include adding at least one of the detection score and the disease score to the first image data.

According to one embodiment, the body part may include at least one of an arm, a leg, an abdomen, a back, a hand, and a foot.

According to various embodiments, provided is a disease information providing method performed by an analysis server including a memory and a processor configured to drive a program loaded from the memory, the method including obtaining first image data, which is obtained by image-capturing a body part and one or more suspicious tissues located in the body part, from an external device, analyzing the first image data, wherein the analysis result is obtained by using an artificial neural network, and the artificial neural network is trained to detect a target tissue related to a disease from the image data obtained by image-capturing the body part, detecting at least one target tissue, in which a disease score obtained from a result value of at least some of a plurality of disease indicators is analyzed to be greater than or equal to a threshold value, from among one or more suspicious tissues included in the first image data on the basis of the analysis result, obtaining position information of the detected target tissue, requesting to obtain second image data on the same body part as the body part, after a predetermined time has passed, obtaining a disease score of a target tissue included in the second image data using the artificial neural network, comparing the disease score of the target tissue in the first image data and the disease score of the target tissue in the second image data located at corresponding positions, on the basis of the position information, and providing disease information on the basis of the comparison result.

According to one embodiment, the plurality of disease indicators may include at least some of a malignant disease indicator, and a benign disease indicator and a pre-malignant disease indicator.

According to one embodiment, the malignant disease indicator may include indicators each reflecting three or more diseases, the benign disease indicator may include indicators each reflecting five or more benign tissues, and the pre-malignant disease indicator may include indicators each reflecting two or more preliminary diseases.

According to one embodiment, the disease score may be generated by combining at least some of a target result value for the malignant disease indicator, a target result value for the pre-malignant disease indicator, and a target result value for the benign disease indicator.

According to one embodiment, in the comparing of the disease scores, a difference between detection score values of target tissues at the same positions included in the first image data and the second image data may be obtained.

According to one embodiment, the disease information providing method may include instructing to capture third image data related to the target tissue on the basis of the comparison result, and outputting a disease score for the target tissue included in the third image data.

According to one embodiment, the disease score may be generated by combining a value obtained by assigning a weight value to the target result value for the malignant disease indicator with a value obtained by assigning a weight value to the target result value for the pre-malignant disease indicator, and the weight value may be selected in a range of more than 0 and less than or equal to 1.

According to one embodiment, in the outputting of the disease score, disease information corresponding to three or more target result values having the largest value or three or more target result values having the largest value is output.

According to one embodiment, the disease information providing method may include providing a reminder indication to a user before the predetermined time has passed.

According to one embodiment, the disease information providing method may further include outputting a body image including a unit body part, and receiving a user input for the unit body part on the basis of the output body image.

According to one embodiment, the disease information providing method may further include determining a disease progression degree of the target tissue on the basis of the comparison result.

According to one embodiment, the disease information providing method may further include detecting, from the third image data, a target tissue that is not present in the first image data.

The method according to the embodiment may be implemented in the form of program commands executable through various computer means and be recorded in a computer-readable medium. The computer-readable medium may include program instructions, data files, data structures, and the like in alone or a combination thereof. The program instructions recorded in the computer-readable medium may be specially designed and configured for the embodiment or may be effective to those skilled in the computer software. Examples of the computer-readable recording media include magnetic media such as a hard disk, a floppy disk, and a magnetic tape, optical recording media such as a compact disc read only memory (CD-ROM) and a digital versatile disc (DVD), a magneto-optical medium such as a floptical disk, and hardware devices specifically configured to store and execute program commands, such as a read only memory (ROM), a random access memory (RAM), a flash memory, and the like. Examples of the program instructions include machine language codes generated by a compiler, as well as high-level language codes which are executable by a computer using an interpreter or the like. The above-described hardware devices may be configured to operate as one or more software modules so as to perform an operation of the embodiment, and vice versa.

According to various embodiments, disease information on a lesion can be accurately and conveniently determined using an artificial neural network trained with image data labeled with a plurality of disease indicators.

The effects of the present disclosure are not limited to the above-described effects, and the effects not mentioned may be clearly understood by a person skilled in the art to which the present disclosure pertains from the present specification and the accompanying drawings.

As is described above, while the present disclosure has been described with reference to the specific embodiments thereof, various changes and modification may be derived by those skilled in the art from the above description. For example, even when the described techniques may be performed in a different order than the described method, and/or elements of the described systems, structures, devices, circuits, and the like may be coupled to combined in other forms, or replaced or substituted by other components or equivalents, appropriate results can be achieved Therefore, other implementations, other embodiments, and equivalents to the appended claims fall within the scope of the following claims.

What is claimed is:

1. A disease information providing method performed by an analysis server including a memory and a processor configured to drive a program loaded from the memory, the method comprising:
   obtaining first image data obtained by image-capturing a body part and one or more suspicious tissues located in the body part;
   analyzing the first image data using an artificial neural network, wherein the first artificial neural network is trained to detect a target tissue related to a disease from the image data obtained by image-capturing the body part;
   detecting one or more target tissues, in which a detection score derived from a result value of at least some of a plurality of disease indicators is analyzed to be greater than or equal to a threshold value, from among the one or more suspicious tissues included in the first image data on the basis of the analysis result;
   requesting second image data on the one or more target tissues;
   obtaining the second image data obtained by image-capturing the one or more target tissues;
   obtaining disease information on the plurality of disease indicators corresponding to the target tissue using a second artificial neural network, wherein the second artificial neural network is trained to obtain a target result value related to the plurality of disease indicators for the target tissue included in the image data; and
   providing a disease score on the basis of the target result value.

2. The method of claim 1, wherein the plurality of disease indicators include at least some of a malignant disease indicator, a benign disease indicator, and a pre-malignant disease indicator.

3. The method of claim 2, wherein
   the malignant disease indicator includes indicators each reflecting three or more diseases,
   the benign disease indicator includes indicators each reflecting five or more benign tissues, and
   the pre-malignant disease indicator includes indicators each reflecting two or more preliminary diseases.

4. The method of claim 2, wherein the disease score is generated by combining at least some of a target result value for the malignant disease indicator, a target result value for the pre-malignant disease indicator, and a target result value for the benign disease indicator.

5. The method of claim 4, wherein
   the disease score is generated by combining a value obtained by assigning a weight value to the target result value for the malignant disease indicator with a value obtained by assigning a weight value to the target result value for the pre-malignant disease indicator, and
   the weight value is selected in a range of more than 0 and less than or equal to 1.

6. The method of claim 2, wherein the detection score is generated by combining a result value for the malignant disease indicator and a result value for the pre-malignant disease indicator.

7. The method of claim 6, wherein
   the threshold value includes a first threshold value and a second threshold value greater than the first threshold value, and
   the method further comprises instructing to provide different indications in a case in which the detection score is greater than or equal to the first threshold value and less than the second threshold value and in a case in which the detection score is greater than or equal to the second threshold value.

8. The method of claim 2, wherein the disease score includes disease information on three indicators having the largest value among the plurality of target result values.

9. The method of claim 1, further comprising adding at least one of the detection score and the disease score to the first image data.

10. The method of claim 1, wherein the body part includes at least one of an arm, a leg, an abdomen, a back, a hand, and a foot.

* * * * *